United States Patent [19]

Bitter et al.

[11] Patent Number: 4,987,273

[45] Date of Patent: Jan. 22, 1991

[54] PROCESS FOR THE SEPARATION OF A PHENOL

[75] Inventors: Johan G. A. Bitter; Johannes L. W. C. den Boestert; Wilhelmus J. M. Weeres, all of Amsterdam, Netherlands

[73] Assignee: Shell Oil Company, Houston, Tex.

[21] Appl. No.: 439,312

[22] Filed: Nov. 21, 1989

[30] Foreign Application Priority Data

Nov. 23, 1988 [GB] United Kingdom ................ 8827306

[51] Int. Cl.$^5$ ............................................. C07C 37/82
[52] U.S. Cl. .................................... 568/758; 568/749; 568/756
[58] Field of Search ........................ 568/756, 758, 749

[56] References Cited

U.S. PATENT DOCUMENTS 4,503,267  3/1985  Paulin ................................. 568/758

FOREIGN PATENT DOCUMENTS 2039499  8/1980  United Kingdom ................ 568/758

Primary Examiner—Werren B. Lone
Attorney, Agent, or Firm—Ronald R. Reper

[57] ABSTRACT

The invention relates to a process for the separation of a phenol from a mixture obtained by the carboxylation of the phenol and containing phenol, phenolate and the carboxylation products thereof, which process comprises separation carried out by selectively absorbing the phenol into the wall of a membrane, solubilizing the phenol in the membrane matrix, diffusing the phenol through the membrane and desorbing the phenol from the other wall.

11 Claims, No Drawings

PROCESS FOR THE SEPARATION OF A PHENOL

BACKGROUND OF THE INVENTION

The invention relates to a process for the separation of a phenol from a mixture obtained by carboxylation of the phenol.

When alkyl-substituted phenols are converted into alkyl salicylates, the yield is generally about 75%. When recycling of the starting alkyl-substituted phenols to the reactor is applied, the yield is increased to about 82%. Since the unreacted alkyl-substituted phenols and the desired alkyl salicylates product are difficult to separate in practice until now, the phenols have not been removed. In the production of overbased calcium salts of the above-mentioned alkylsalicylic acids, the phenols presence in the product may be tolerated for many applications. It would, however, be preferable if the alkyl-substituted phenols could be separated and used again as starting materials in the preparation of alkyl salicylates. In the overall reaction much higher yields of alkyl salicylates could be obtained, calculated on the alkyl phenols.

Applicant has now found that these phenols can be separated from said salicylates by the use of a certain membrane which selectively absorbs the phenols.

SUMMARY OF THE INVENTION

The invention relates to a process for the separation of a phenol from a mixture obtained by the carboxylation of the phenol and containing phenol, phenolate and the carboxylation products therefrom which process comprises selectively absorbing the phenol into a first side of a membrane wall, solubilizing the phenol within said membrane, diffusing the phenol through the membrane, and desorbing the phenol from the second side of said membrane wall.

The invention further provides a process for the manufacture of alkyl salicylates from alkyl phenols, which process comprises:

(a) reacting an alkyl phenol with an alkali metal hydroxide to form an alkali metal phenate;

(b) reacting said alkali metal phenate product from step (a) in a reaction zone with carbon dioxide to obtain a carboxylated product mixture comprising alkali metal salicylate;

(c) passing said product from step (b) as feed to a reverse osmosis zone;

(d) subjecting said feed to reverse osmosis to obtain a retentate having higher content of alkali metal salicylate than said feed, and a permeate stream containing at least part of the alkali metal phenate content of said feed; and (e) recycling at least part of said permeate stream to the reaction zone of step (b).

ILLUSTRATIVE EMBODIMENT

The alkyl salicylates can be prepared by the following sequence of reactions: alkylation, phenation, carboxylation and equilibration. These reactions may be illustrated as follows:

1. Alkylation

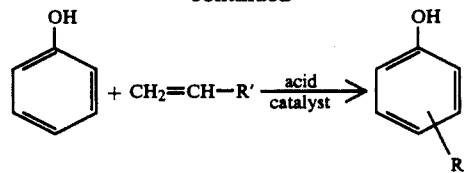

wherein R' is an alkyl group, having 2 carbon atoms less than R.

2. Phenation

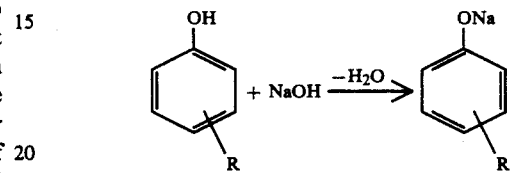

3. Carboxylation

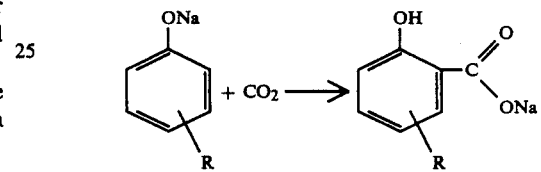

4. Furthermore the following equilibrium reaction occurs:

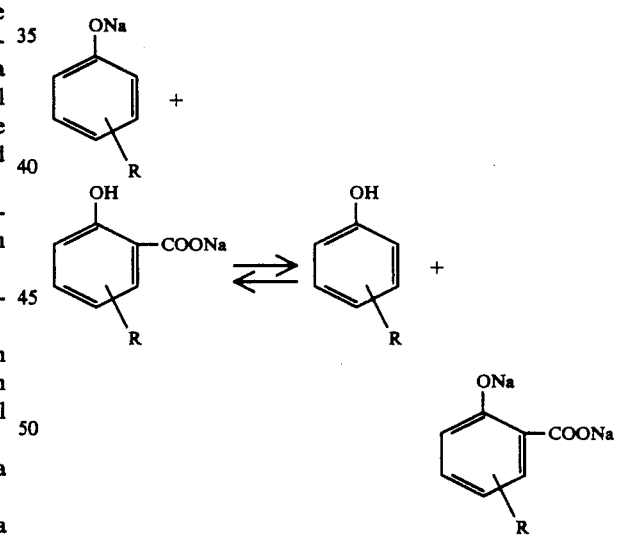

R is preferably an alkyl group having from 2 to 20 carbon atoms, more preferably from 10 to 18 carbon atoms.

The alkylated phenol prepared during the alkylation reaction preferably contains a mixture of alkyl groups and may even contain up to 20% of dialkylated compounds, depending upon the reaction circumstances.

When the equilibrium reaction mixture of 4 is purified by means of a membrane, the equilibrium reaction is shifted to the right, since the alkyl-substituted phenol is withdrawn through osmosis.

To prepare an overbased calcium alkyl salicylate the following reactions may take place.

5. Acidification

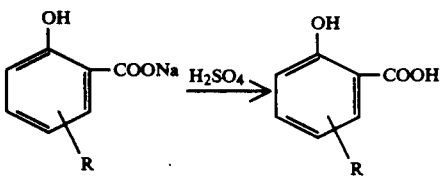

6. Neutralization with Ca

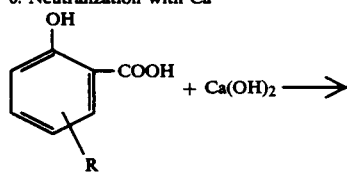

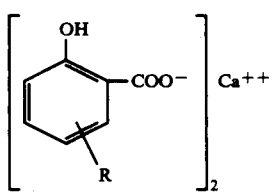

7. Overbasing with Ca(OH)$_2$ + CO$_2$

The phenation and carboxylation under 2 and 3 are preferably carried out in the presence of a solvent, such as an aromatic hydrocarbon. Examplary aromatic hydrocarbons are benzene, toluene and o-, m-, or p-xylene and mixtures thereof. In the phenation reaction, KOH can be applied instead of NaOH. The solvents, especially the xylenes, may serve as swelling agents for the membranes.

Membranes are very well described in Kirk-Othmer *Enclyclopedia of Chemical Technology*, third edition, part 15, page 92, etc.

A very important and fundamental means by which a species can be transported through a membrane involves dissolving of the permeate molecules (alkylated phenols) into the membrane at its upstream surface, followed by molecular diffusion down its concentration gradient to the downstream face of the membrane. There the alkylated phenol is dissolved into its adjacent fluid phase.

The driving force for diffusion through the membrane is the pressure exerted to the system. Another driving force is the concentration. In fact, it is the pressure difference and the concentration difference on both sides of the membrane which constitute the driving force.

Preferred membranes used in the process according to the invention are the dense cross-linked elastomeric membranes such as polyisoprene, polybutadiene, polydimethylsiloxane and fluorosilicon rubbers. Dense membranes generally may have, however, low transport rates. To attain acceptable transport rates, it is necessary to make the membranes thin, preferably very thin.

It may therefore be advantageous to bring the dense membranes on a porous support. The pressure exerted on the upstream face of the membrane is generally in the range of from 10 to 100 bar (100 to 10,000 kPa) during the separation step. The temperature, used in the process according to the invention, ranges between 0° C. and 120° C., preferably from 50° C. to 90° C.

Of special importance to be used as membranes are the organopolysiloxanes, such as polydimethylsiloxane.

Only a part of the total flux through the membrane is alkyl phenol. The permeate may be recirculated to the reactor or to the distillation column in the caustic reaction of the alkyl phenol.

The membrane is highly selective for alkyl phenol, since no sodium is found in the permeate.

The amount of alkyl phenol in the carboxylated alkyl phenol product (sodium alkyl salicylate) can be considerably reduced. The alkyl phenol can be used again in the carboxylation reaction. The xylene from the permeate, consisting of xylene and alkyl phenol, can be distilled off and used either in the phenation reaction or as a swelling agent for the membrane separation process.

EXAMPLE I

Caustic alkyl phenol, containing $C_{14}$–$C_{18}$ alkyl groups, was admixed with xylene and the mixture was heated, so that an azeotropic mixture of xylene and water was distilled off. The azeotropic mixture was collected and separated in water and xylene. The xylene was recirculated to the caustic alkyl phenol xylene mixture. The alkyl phenol was led into a reactor in which it was reacted with carbon dioxide in a xylene solution. The obtained reaction product comprising alKyl phenol and sodium alkyl salicylate together with xylene was used in the experiment.

A solution of alkyl phenol and sodium in xylene was pumped along the high pressure side of a polydimethylsiloxane membrane with an area of 10.2 cm$^2$, at a temperature of 60° C. and at permeation pressures between 5 and 40 bar (500 and 4000 kPa). The pressure was maintained via an air pressurized bellow and recirculation of the retentate solution was achieved via a rotary pump. The permeate solution was collected at the downstream side of the membrane and was not recirculated.

A feed consisting of 75.5% by weight of xylene and 24.5% by weight of alkyl phenol and sodium alkyl salicylate together (with an alkyl phenol/sodium salicylate weight ratio of 0.21) gave after six hours a retentate consisting of 66.4% by weight of xylene and 33.6% by weight of alkyl phenol and sodium together (with a weight ratio of alkyl phenol sodium alky salicylate of 0.18). The permeate contained 94.5% by weight of xylene and 5.5% by weight of alkyl phenol. No sodium alkyl salicylate was found in the permeate.

The pressure, to which the membrane was subjected, was 5 bar during the first three hours, 20 bar at three hours to four hours and 40 bar the last two hours (at 4 hrs to 6 hrs), respectively. Every hour the flux was measured. The total flux through the polydimethylsiloxane membrane was 400 l/m$^2$.day, 1100 l/m$^2$.day and 1400 l/m$^2$.day at a pressure of 5, 20 and 40 bar, respectively.

The alkyl phenol flux through the polydimethylsiloxane membrane was at the beginning of the experiment 140 l/m$^2$.day, but decreased to 60 l/m$^2$.day at 5 bar pressure. Increasing the pressure to 20 bar and 40 bar led to an alkyl phenol flux of 70l/m$^2$.day and 80 l/m$^2$.day, respectively. Consequently, increase in pressure lead to a moderate increase in alkyl phenol flux, but to a considerable increase in xylene flux. A highly selective separation of alkyl phenol was obtained, since no sodium alkyl salicylate could be detected in the permeate.

EXAMPLE II

A feed consisting of 69.4% by weight of xylene and 30.6% by weight of alkyl phenol and sodium together was pumped along the high pressure side of the polydimethylsiloxane membrane with an area of 10.2 cm$^2$ at a temperature of 60° C. and at a pressure of 20 bar (2000 kPa). The pressure was maintained via an air pressurized bellow and the recirculation of the retentate solution was achieved via a rotary pump. The permeate solution was collected at the downstream side of the membrane outside the recirculation system. The experiment lasted about four days. During the experiment the xylene concentration in the feed was held between 63 and 87% by weight of the feed by supplying fresh xylene to the feed at intervals. The reason for this measure being that xylene diffuses through the membrane at a high rate (compared with the alkyl phenol rate).

In the following table the results are given:

TABLE

| Time (hr) | Xylene Concentrate Feed (% w) | AF*/AS** (mol/mol) in Feed | AF Concentrate (% w) | AS Concentrate (% w) | Xylene Concentrate Permeate (% w) | Total Flux (l/m$^2$ · day) | AF Flux (l/m$^2$ · day) |
|---|---|---|---|---|---|---|---|
| 0.00 | 69.39 | 0.20 | 16.67 | 83.33 | 92.40 | 1210.00 | 91.96 |
| 19.42 | 63.60 | 0.15 | 13.00 | 86.97 | 93.00 | 910.00 | 63.70 |
| 19.42 | 75.60 | 0.14 | 12.28 | 87.70 | | | |
| 43.70 | 66.10 | 0.09 | 8.26 | 91.74 | 94.20 | 856.00 | 49.65 |
| 67.80 | 87.80 | 0.10 | 8.30 | 91.70 | | | |
| 90.98 | 67.80 | 0.08 | 7.40 | 92.50 | 97.40 | 739.50 | 19.23 |

*Alkyl phenol.
**Sodium alkyl salicylate.

None of the permeates contained sodium alkyl salicylate acid, consequently the polydimethylsiloxane membrane is highly selective to alkyl phenol. After about four days the alkyl phenol concentration in the original feed mixture is considerably reduced.

What is claimed is:

1. A process for the separation of a phenol from a product mixture obtained by the carboxylation of the phenol and containing phenol, an alkali metal phenolate and the carboxylation products therefrom which process comprises at a temperature in the range between 0° C. and 120° C. selectively absorbing the phenol into a first, upstream side of a membrane wall of dense cross-linked elastomer selected from polyisoprene, polybutadiene, organopolysiloxane and fluorosilicon rubbers selectively permeable for phenol while solubilizing the phenol within said membrane, applying pressure to said product mixture on said upstream side of said membrane thereby diffusing said phenol through the membrane, and desorbing the phenol from the second side of said membrane wall.

2. A process according to claim 1 wherein said product mixture comprises an alkyl-substituted phenol having at least one alkyl group of from 2 to 20 carbon atoms.

3. A process according to claim 2 wherein said at least one alkyl group has from 10 to 18 carbon atoms.

4. A process according to claim 1 wherein said product mixture comprises phenolate sodium or potassium phenolate.

5. A process according to claim 1 wherein said membrane is organopolysiloxane.

6. A process according to claim 5 wherein said membrane is a polydimethylsiloxane.

7. A process according to claim 1 wherein said product mixture contains an aromatic hydrocarbon swelling agent.

8. A process according to claim 7 wherein said swelling agent is a xylene.

9. A process for the manufacture of alkyl salicylcates from alkyl phenols at a temperature between 0° C. and 120° C., which process comprises:

(a) reacting an alkyl phenol with an alkali metal hydroxide to form an alkali metal phenate;

(b) reacting said alkali metal phenate product from step (a) in a reaction zone with carbon dioxide to obtain a carboxylated product mixture comprising alkali metal salicylate;

(c) passing said product from step (b) as feed to a reverse osmosis zone;

(d) subjecting said feed to reverse osmosis to obtain a retentate having higher content of alkali metal salicylate than said feed, and a permeate stream containing at least part of the alkali metal phenate content of said feed; and (e) recycling at least part of said permeate streams to the reaction zone of step (b).

10. A process according to claim 1 wherein in step (d) the applied pressure during reverse osmosis is in the range of from 10 to 100 bar (100 to 10,000 kPa).

11. A process according to claim 9 wherein in step (d) the temperature during reverse osmosis is in the range of from 50° C. to 90° C.

* * * * *